(12) United States Patent
Liang et al.

(10) Patent No.: US 11,196,086 B2
(45) Date of Patent: Dec. 7, 2021

(54) LITHIUM ION BATTERY AND RELEVANT BATTERY MODULE, BATTERY PACK AND APPARATUS

(71) Applicant: Contemporary Amperex Technology Co., Limited, Ningde (CN)

(72) Inventors: Chengdu Liang, Ningde (CN); Cuiping Zhang, Ningde (CN); Ming Zhang, Ningde (CN); Peipei Chen, Ningde (CN); Hailin Zou, Ningde (CN); Liye Li, Ningde (CN)

(73) Assignee: Contemporary Amperex Technology Co., Limited, Ningde (CN)

( * ) Notice: Subject to any disclaimer, the term of this patent is extended or adjusted under 35 U.S.C. 154(b) by 0 days.

(21) Appl. No.: 17/131,803

(22) Filed: Dec. 23, 2020

(65) Prior Publication Data
US 2021/0119260 A1  Apr. 22, 2021

Related U.S. Application Data

(63) Continuation of application No. PCT/CN2020/100702, filed on Jul. 7, 2020.

(30) Foreign Application Priority Data

Jul. 9, 2019 (CN) .......................... 201910613567.9

(51) Int. Cl.
*H01M 10/0568* (2010.01)
*H01M 10/0525* (2010.01)
(Continued)

(52) U.S. Cl.
CPC ....... *H01M 10/0568* (2013.01); *C07C 311/48* (2013.01); *C07D 327/00* (2013.01);
(Continued)

(58) Field of Classification Search
CPC ......... H01M 10/0568; H01M 10/0525; H01M 10/0567; H01M 10/0569; H01M 4/525
See application file for complete search history.

(56) References Cited

U.S. PATENT DOCUMENTS

2008/0096112 A1* 4/2008 Ihara ................. H01M 10/0569
429/338

FOREIGN PATENT DOCUMENTS

| CN | 101783412 A | 7/2010 |
|---|---|---|
| CN | 102024983 A | 4/2011 |

(Continued)

OTHER PUBLICATIONS

PCT International Search Report for PCT/CN2020/100702, dated Sep. 29, 2020, 13 pages.

(Continued)

*Primary Examiner* — Osei K Amponsah
(74) *Attorney, Agent, or Firm* — Law Offices of Liaoteng Wang

(57) ABSTRACT

The present application relates to a lithium ion battery, comprising: a positive electrode plate, a negative electrode plate, a separator disposed between the positive electrode plate and the negative electrode plate, and an electrolytic solution, the positive electrode plate including a positive electrode current collector and a positive electrode active material layer provided on at least one side of the positive electrode current collector, and the electrolytic solution including an organic solvent, a lithium salt and an additive, wherein the lithium salt comprises a primary lithium salt, the primary lithium salt is a first compound in an amount of 30% or more relative to the total molar amount of the lithium salt, and the first compound has a structure represented by the following formula I, and wherein the additive comprises a second compound represented by the following formula II.

(Continued)

(Formula I)

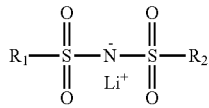

(Formula II)

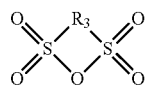

9 Claims, 4 Drawing Sheets

(51) Int. Cl.
*H01M 10/0567* (2010.01)
*H01M 10/0569* (2010.01)
*H01M 4/525* (2010.01)
*C07C 311/48* (2006.01)
*C07D 327/00* (2006.01)
*H01M 4/02* (2006.01)

(52) U.S. Cl.
CPC ....... *H01M 4/525* (2013.01); *H01M 10/0525* (2013.01); *H01M 10/0567* (2013.01); *H01M 10/0569* (2013.01); *H01M 2004/028* (2013.01); *H01M 2300/0025* (2013.01)

(56) References Cited

FOREIGN PATENT DOCUMENTS

| | | |
|---|---|---|
| CN | 101783412 B | 1/2013 |
| CN | 103515648 A | 1/2014 |
| CN | 107408728 A | 11/2017 |
| CN | 105304936 B | 5/2018 |
| CN | 108336397 A | 7/2018 |
| EP | 3163664 | 5/2017 |
| EP | 3240093 A1 | 11/2017 |

OTHER PUBLICATIONS

The extended European search report dated Aug. 25, 2021 for European Application No. 20824413.7, 5 pages.

\* cited by examiner

LITHIUM ION BATTERY AND RELEVANT BATTERY MODULE, BATTERY PACK AND APPARATUS

CROSS-REFERENCE TO RELATED APPLICATION

This application is a continuation of International Application No. PCT/CN2020/100702, filed on Jul. 7, 2020, which claims priority to Chinese Patent Application No. 201910613567.9 entitled "lithium ion battery" and filed on Jul. 9, 2019, both of which are incorporated herein by reference in their entireties.

TECHNICAL FIELD

The present application relates to the field of electrochemical technology, and more particularly, to a lithium ion battery.

BACKGROUND

Lithium-ion batteries have attracted much attention due to their high specific energy, long cycle life, low self-discharge, and good safety performance. At present, the application of lithium-ion batteries has penetrated into all aspects of daily life such as cameras, notebook computers, and electric vehicles.

As market demand for batteries with high energy density increases, the development of batteries with high energy density is imminent. At present, there are two ways to improve battery energy density: (1) to use high nickel ternary materials to replace traditional lithium cobalt positive materials, and (2) to increase battery charging voltage. However, the application of these two schemes inevitably has an adverse effect on the electrolytic solution. For example, the high nickel ternary material enables the positive electrode plate to have a reduced stability due to an increased nickel content. Therefore, during the cyclic storage process, the positive electrode/electrolytic solution interface is unstable, resulting in continuous oxidation and decomposition of the electrolytic solution on the positive electrode. By increasing the battery charging voltage, the positive electrode potential is raised during charging, and the electrolytic solution is more likely to be oxidized and decomposed. In other words, the above two approaches will lead to increased oxidation and decomposition of the electrolytic solution. When the above mentioned events occur, on the one hand, gas will be generated, which will increase the physical distance between the positive and negative electrodes, increase the electrolytic solution concentration polarization, and further induce side reactions in the electrolytic solution, resulting in poor battery cycle performance; on the one hand, the by-products produced by oxidation and decomposition of electrolytic solution will cover the electrode/electrolytic solution interface, causing the solid electrolytic solution interface (SEI) film to continue to thicken and the interface impedance to increase, thereby deteriorating the power performance of the battery.

SUMMARY

An object of the present application is to provide a lithium-ion battery in the form of a high-energy system (especially in the form of a high-nickel system) that can work at a high charging voltage. In order to achieve the above objective, in one aspect of the present application, a lithium ion battery is provided, including: a positive electrode plate, a negative electrode plate, a separator spaced between the positive electrode plate and the negative electrode plate, and an electrolytic solution, the positive electrode plate including a positive electrode current collector and a positive electrode active material layer provided on at least one side of the positive electrode current collector, and the electrolytic solution including an organic solvent, a lithium salt and an additive, wherein the lithium salt includes a primary lithium salt, the primary lithium salt is a first compound in an amount of 30% or more relative to the total molar amount of the lithium salt, and the first compound has a structure represented by the following formula I:

(Formula I)

in which formula I, $R_1$ and $R_2$ each independently represent a fluorine atom, a fluoroalkyl group having 1-20 carbon atoms, or a fluoroalkoxy group having 1-20 carbon atoms, and wherein the additive includes a second compound represented by the following formula II, (Formula II)

in which formula II, $R_3$ represents an alkylene group having 2-4 carbon atoms, a fluoroalkylene group having 2-4 carbon atoms, an alkyl-substituted alkylene group having 2-4 carbon atoms, an alkenylene group having 2-4 carbon atoms, a fluoroalkenylene group having 2-4 carbon atoms, an alkyl-substituted alkenylene group having 2-4 carbon atoms, an arylene group having 6-14 carbon atoms, and a fluorinated arylene group having 6-14 carbon atoms or an alkyl-substituted arylene group having 6-14 carbon atoms.

The inventors of the present application have surprisingly found that the electrolytic solution as formulated by using the first compound as a primary lithium salt constituting 30 mol % or more, preferably 50 mol % or more of the total molar amount of the lithium salt and compounding it with the second compound as an additive can effectively improve the power performance and high-temperature storage performance of the high nickel system simultaneously, which was difficult to foresee prior to this application.

Without being bound by any theory, the inventors provide the following explanations so as to better understand the present application.

In the lithium ion battery according to the present application, the first compound is used as a primary lithium salt in the electrolytic solution, that is, its content accounts for 30 mol % or more of the total molar amount of the lithium salt, preferably 50 mol % or more of the total molar amount of the lithium salt. The first compound is more stable than conventional lithium salts such as lithium hexafluoroborate, which is not sensitive to water and temperature, thereby making the electrolytic solution more stable to a certain extent, but it also has improved conductivity, thereby improving the powder performance of the electrolytic solution. Moreover, compared with the conventional lithium salt, the first compound as a primary lithium salt can also avoid the problem of reduced gas production performance during high-temperature storage caused by poor film forming effect on the positive electrode when these conventional lithium salts are used as a primary lithium salt.

According to the lithium ion battery of the present application, the electrolytic solution further comprises the second compound as an additive. The additive works as follows during the charging and discharging process of batteries: during the charging process, the second compound will be reduced and decomposed into sulfur-containing compounds, some of which reduced and decomposed products will be deposited on the negative electrode interface and participate in film formation, thereby inhibiting decomposition of the electrolytic solution, and another part of which reduced and decomposed products will migrate into the positive electrode, and enable the positive electrode active material to have reduced reactive activity, thereby inhibiting the oxidative decomposition of the electrolytic solution caused by the instability of the positive electrode active material, reducing storage gas generation, and also cover the exposure point of the positive electrode current collector, thereby protecting the positive electrode current collector, especially the aluminum positive electrode current collector, from being corroded by the first compound.

The combination of the above two compounds produces a synergistic effect. Therefore, the electrolytic solution according to the present application can effectively improve the power performance and high-temperature storage gas production performance of lithium-ion batteries simultaneously, and can even improve the power performance and high-temperature storage gas production performance of high-nickel lithium-ion batteries working at high charging voltages simultaneously.

In another aspect, the present application provides a battery module comprising the above mentioned lithium ion battery.

In yet another aspect, the present application provides a battery pack comprising the above mentioned battery module.

In still yet another aspect, the present application provides an apparatus comprising the above mentioned lithium ion battery, wherein the lithium ion battery is used as a power source of the apparatus; preferably, the apparatus comprising electric vehicles, hybrid electric vehicles, plug-in hybrid electric vehicles, electric bicycles, electric scooters, electric golf carts, electric trucks, electric ships, or energy storage systems.

The details of one or more embodiments of the present application are set forth in the following description. According to the specification and claims, other features, purposes and advantages of this application will become apparent.

In above figures, the denotation of the reference numerals is as follows: 1—battery pack; 2—upper cabinet body; 3—lower cabinet body; 4—battery module; 5—battery; 51—case; 52—electrode assembly; and 53—top cover assembly.

DEFINITION

In the content of the present application, when "a", "an", "the", "at least one", and "one or more" something are used, it should be interpreted as having both singular and plural numbers, unless otherwise stated or clearly contradictory to the context.

Throughout the present invention, where compositions are described as having, including, or comprising specific components or fractions, or where processes are described as having, including, or comprising specific process steps, it is contemplated that the compositions or processes as disclosed herein may further comprise other components or fractions or steps, whether or not, specifically mentioned in this invention, as along as such components or steps do not affect the basic and novel characteristics of the invention, but it is also contemplated that the compositions or processes may consist essentially of, or consist of, the recited components or steps.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As used herein, the term "primary lithium salt" refers to a lithium salt that exerts a main function in the electrolytic solution, and its content usually accounts for 30 mol % or more of the total molar amount of lithium salt, preferably its content accounts for 50 mol % or more of the total molar amount of lithium salt.

As used herein, the term "secondary lithium salt" refers to a lithium salt that exerts a minor function in the electrolytic solution. For example, it may be used to reduce the cost of the electrolytic solution. Generally, its content accounts for 50 mol % or less, for example 40 mol % or less, 30 mol % or less, 20 mol % or less of the total molar amount of the lithium salt.

In the context of describing a group or compound herein, the term "fluoro" refers to a group or compound in which one or more hydrogen atoms are replaced by fluorine atoms. Preferably, fluoro refers to perfluoro or partially fluoro. For example, fluoromethyl includes but not limited to —$CF_3$, —$CHF_2$, and —$CH_2F$.

In the present application, the phrase "the ratio of the mass of the second compound to the total area S ($m^2$) of the positive electrode current collector" refers to the ratio of the mass of the second compound (in g) and the effective area of the positive electrode current collector (in $m^2$), which usually is usually calculated based on the actual battery cell size and the actual electrolytic solution amount as used. In some embodiments of the present application, the areal density of the second compound on the current collector of the positive electrode plate is in the range of 0.1 g/m² to 3.1 g/m².

When used in the context of the first compound, the term "corrosion potential" refers to a potential as measured when a metal reaches a stable corrosion state in the presence of the first compound without an external current, which is a parameter used to measure the corrosion ability of the first compound to the electrode plate of a lithium ion battery. Generally, the higher the corrosion potential, the stronger the corrosion ability of the first compound is.

When used in the context of a second compound, the term "reduction potential" is a parameter used to measure the reducing ability of the second compound. Generally, the higher the reduction potential, the stronger the reducing ability of the second compound.

The phrase "the difference between the corrosion potential of the first compound to the positive electrode current collector and the reduction potential of the second compound" is a parameter used to measure the relationship between the corrosion ability of the first compound to the positive electrode current collector and the reducing ability of the second compound. In the present application, it is desired that the gap between the corrosion ability of the first compound and the reducing ability of the second compound should not be too large, which would be better to keep within a certain range. In some embodiments of the present application, the difference between the corrosion potential of the first compound to the positive current collector and the reduction potential of the second compound is between 2.7 and 4.2.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

DETAILED DESCRIPTION

The lithium ion battery according to the present application will be described in detail below.

The lithium ion battery according to the present application comprises a positive electrode plate, a negative electrode plate, a separator spaced between the positive electrode plate and the negative electrode plate, and an electrolytic solution, the positive electrode plate comprising a positive electrode current collector and a positive electrode active material layer provided on at least one side of the positive electrode current collector, and the electrolytic solution including an organic solvent, a lithium salt and an additive, wherein the lithium salt comprises as a primary lithium salt a first compound having a structure represented by the following formula I:

(Formula I)

in which formula, $R_1$ and $R_2$ each independently represent a fluorine atom, a fluoroalkyl group having 1-20 carbon atoms, or a fluoroalkoxy group having 1-20 carbon atoms.

In the above general formula I, in the fluoroalkyl group with 1-20 carbon atoms, the number of fluorine atoms and the substitution position thereof are not particularly limited. According to actual demand, the fluorine atom may be selected to replace some of the hydrogen atoms or all of the hydrogen atoms in the alkyl group. For example, the number of fluorine atom may be one, two, three, four or more.

As examples of fluoroalkyl groups, fluoromethyl, 2-fluoroisobutyl, 2-fluoroethyl, 1-fluoroethyl, 3-fluoro-n-propyl, 2-fluoroisopropyl, 4-fluoro-n-butyl, 3-fluoro-sec-butyl, 2-fluoro-sec-butyl, 5-fluoro-n-pentyl, 1-fluoro-n-pentyl, 4-fluoroisopentyl, 3-fluoroisopentyl, 6-fluoro-n-hexyl, 4-fluoro-isohexyl, 7-fluoro-n-heptyl, 8-fluoro-n-octyl, 1,2-difluoroethyl, difluoromethyl, trifluoromethyl, pentafluoroethyl, perfluoroisopropyl, perfluorobutyl, perfluorocyclohexyl, and the like may be used.

In the above-mentioned general formula I, the kind and number of the alkoxy group attached to fluorine atom in the fluoroalkoxyl group having 1 to 10 carbon atoms are not particularly limited and may be selected depending on the actual requirements such as the chain alkoxyl group and the cycloalkoxyl group, wherein the chain alkoxyl group further comprises a straight alkoxyl group and a branched alkoxyl group. In the alkoxyl group, the number of oxygen atom is preferably 1 or 2. In addition, the number of fluorine atom attached to the alkoxy group may be 1, 2, 3, 4, 5 or 6.

As examples of fluoroalkoxy groups, fluoromethoxy, 2-fluoroethoxy, 3-fluoro-n-propoxy, 2-fluoroisopropoxy, 4-fluoro-n-butoxy, 3-fluoro-sec-butoxy, 5-fluoro-n-pentyloxy, 4-fluoroisopentyloxy, 3-fluoro-tert-pentyloxy, 3-fluoro-2,2-dimethylpropoxy, 3-fluoro-1-ethylpropoxy, 4-fluoro-1-methylbutoxy, 6-fluoron-hexyl oxy, 5-fluoro-isohexyloxy, 3-fluoro-1,1,2-trimethylpropoxy, 2,2,2-trifluoroethoxy, 2,2,3,3,3-pentafluoro-propoxy, 2,2,3,3-tetrafluoropropoxy, $OCH(CF_3)_2$, and the like may be used.

Preferably, the first compound is selected from one or more of lithium bis(fluorosulfonyl)imide, lithium fluorosulfonyl (trifluoromethylsulfonyl) imide, lithium bis(trifluoromethylsulfonyl)imide, lithium methylsulfonyl(trifluoromethylsulfonyl) imide, lithium trifluoromethanesulfonyl (pentafluoroethylsulfonyl) imide, lithium bis (pentafluoroethylsulfonyl)imide, $LiN(SO_2OCH_2CF_3)_2$, $LiN(SO_2OCH_2CF_2CF_3)_2$, $LiN(SO_2OCH_2CF_2CF_2H)_2$, $LiN[(SO_2OCH(CF_3)_2]$, preferably selected from one or two of lithium bis(fluorosulfonyl) imide and lithium methylsulfonyl(trifluoromethanesulfonyl) imide, more preferably selected from lithium bis(fluorosulfonyl)imide.

According to the present application, the first compound is present in an amount of 30 mol % or higher, preferably 40 mol % or higher, more preferably 50 mol % or higher, such as 60 mol % or higher, 70 mol % or higher, or 80 mol % or higher, or even 90 mol % or higher relative to the total molar amount of lithium salt in the electrolytic solution. Using the first compound in this application as a primary lithium salt has achieved very beneficial effects. Due to the inherent structural characteristics of the fluorine-containing sulfonimide lithium salt, it has higher conductivity at room temperature, and is more stable than conventional lithium salt (LiPF6), and has lower sensitivity to water and temperature, so it can be used to improve the stability and power performance of the electrolytic solution. However, considering practical application, the content of the first compound usually should not be too high. Otherwise it will be corrosive to the current collector, especially the aluminum current collector. Moreover, when the first compound is used in a high-nickel lithium-ion battery operating at a high voltage, it is prone to oxidation and decomposition, especially when stored at a high temperature.

The electrolytic solution for lithium ion batteries according to the present application also comprises a secondary lithium salt and the secondary lithium salt is selected from one or more of lithium hexafluorophosphate, lithium tetrafluoroborate, lithium trifluoromethanesulfonate, lithium hexafluoroarsenate, lithium bisoxalate borate and lithium perchlorate, preferably selected from one or two of lithium hexafluorophosphate and lithium tetrafluoroborate, and more preferably selected from lithium hexafluorophosphate.

In some embodiments of the present application, the molar ratio of the primary lithium salt and the secondary lithium salt is in the range of 5:5 to 9:1, preferably in the range of 6:4 to 8:2, for example, 9:1, 8:2, or 7:3.

The inventor found through research that when the content of the fluorine-containing sulfonimide lithium salt is small, it is impossible to effectively improve the conductivity of the electrolytic solution; and when the content is too large, the aluminum foil will be corroded by the high-concentration lithium salt. In the electrolytic solution for lithium ion batteries of the present application, when the first charge occurs, a part of the secondary lithium salt will decompose to produce fluoride ion, and the fluoride ion react with the aluminum foil as the current collector to form an aluminum fluoride passivation layer, thereby inhibiting corrosion of the aluminum foil. Through research, it is found that when the secondary lithium salt is present in an amount of 10 mol % or more based on the total weight of the lithium salt, the corrosion of the first compound to the aluminum foil can be effectively inhibited. However, the amount of the secondary lithium salt should not be too high. When used as a primary lithium salt, it will deteriorate the high-temperature storage gas production performance. Therefore, in the electrolytic solution of the present application, the first compound as the primary lithium salt and the above fluorine-containing inorganic lithium salt as the secondary lithium salt can ensure that the conductivity and power performance of the electrolytic solution and the performance of aluminum foil corrosion keep balance, which is the best strategy to balance performances and cost.

Preferably, the total concentration of the lithium salt in the electrolytic solution may be 0.5 mol/L-1.5 mol/L, more preferably 0.8 mol/L-1.2 mol/L. For example, the total concentration of the total lithium salt in the electrolytic solution may be about 1.0 mol/L.

The lithium ion electrolytic solution according to the present application further comprises an additive, and the additive comprises a second compound represented by the following formula II, (Formula II)

in which formula, $R_3$ represents an alkylene group having 1-4 carbon atoms, a fluoroalkylene group having 1-4 carbon atoms, an alkenylene group having 2-4 carbon atomes, a fluoroalkenylene group having 2-4 carbon atoms, an arylene group having 6 to 14 carbon atoms and a fluoroarylene group having 6 to 10 carbon atoms.

In the above general formula II, the alkylene group having 1 to 4 carbon atoms is a linear or branched alkylene group. Examples of alkylene groups comprise methylene, ethylene, propylene, isopropylene, butylene, isobutylene, sec-butylene, 1-methylpropylene, 2-methyl propylene, and the like.

In the above general formula II, in the fluoroalkylene group with 1-4 carbon atoms, the number of fluorine atoms and the substitution position thereof are not particularly limited. According to actual demand, the fluorine atom may be selected to replace some of the hydrogen atoms or all of the hydrogen atoms in the alkylene group. For example, the number of fluorine atom may be one, two, three, four or more.

Examples of fluoroalkylene groups comprise 1-fluoromethylene, 1-fluoroethylene, 1,1,2,2-tetrafluoroethylene, 1-fluoropropylene, 2-fluoropropylene, 1,1,1-trifluoropropylene, 1-fluoroisopropylene, 1-fluorobutylene, 1-fluoroisobutylene, 1-fluorosec-butylene, and the like.

In the above general formula II, the alkenylene group having 2 to 4 carbon atoms is a straight chain or branched chain alkenylene group, preferably a straight chain alkenylene group, in which the number of double bonds in the alkenylene group can be 1 or 2. Specific examples of alkenylene groups may comprise vinylene, allylidene, isopropenylene, butenylene, butadienylene, 1-methylvinylene, and 1-methylpropenylene, 2-methylpropenylene, and the like.

In the above general formula II, in the fluoroalkenylene group with 2-4 carbon atoms, the number of fluorine atoms and the substitution position thereof are not particularly limited. According to actual demand, the fluorine atom may be selected to replace some of the hydrogen atoms or all of the hydrogen atoms in the alkenylene group. For example, the number of fluorine atom may be one, two or more.

Specific examples of fluoroalkenylene groups may comprise 1-fluorovinylidene, 1,2-difluorovinylidene, 1-fluoroallylidene, 1-fluoroisopropenylene, 1-fluorobutenylene, 1-fluorobutadienylene, 1,2,3,4-tetrafluorobutadienylene, etc.

In the above general formula II, in the arylene group having 6-10 carbon atoms, the specific type of the arylene group is not particularly limited, and can be selected according to actual needs, such as phenylene, naphthylene, and alkyl-phenylene in which other substituent groups may be attached to the phenyl group, such as an alkyl group.

Specific examples of arylene groups may comprise phenylene, benzylidene, 1-naphthylene, 2-naphthylene, o-methylphenylene, m-methylphenylene, p-methylphenylene, p-ethylphenylene, m-ethylphenylene, o-ethylphenylene, 1-tetrahydronaphthylene, 2-tetrahydronaphthylene, 4-vinylphenylene, 3-isopropylphenylene, 4-isopropylphenylene, 4-butylphenylene, 4-isobutylphenylene, 4-tert-butylphenylene, 2,3-dimethylphenylene, 2,4-dimethylphenylene, 2,5-dimethylphenylene, 2,6-dimethylphenylene, 3,4-dimethylphenylene, 3,5-dimethylphenylene, 2,4,5-trimethylphenylene, 2,4,6-trimethyl phenylene, and the like.

In the above general formula II, in the fluoroarylene group with 6-10 carbon atoms, the number of fluorine atoms and the substitution position thereof are not particularly limited. The number of fluorine atom may be one, two, three, four, five or more.

Specific examples of fluoroarylene groups may comprises 2-fluorophenylene, 3-fluorophenylene, 4-fluorophenylene, 2-fluoro-4-methylphenylene, 3-fluoro-4-methyl phenylene, 4-fluoro-2-methylphenylene, 2,4-difluorophenylene, 3,4-difluorophenylene, 2,6-difluoro-4-methylphenylene, 2, 6-difluoro-3-methylphenylene, 2-fluoro-naphthylene, 4-fluoronaphthylene, 2,4,6-trifluorophenylene, 2,3,4,6- tetrafluorophenylene, 4-trifluoromethylphenylene, 2,3,4,5-tetrafluorophenylene, pentafluorophenylene, 3,5-bis(trifluoromethyl)phenylene and the like.

Preferably, the second compound is selected from one or more of the following compounds:

The above second compound works as follows during the charging and discharging process of batteries. During the charging process, the second compound will be reduced and decomposed into sulfur-containing compounds, some of which reduced and decomposed products will be deposited on the negative electrode interface and participate in film formation, thereby inhibiting decomposition of the electrolytic solution, and another part of which reduced and decomposed products will migrate into the positive electrode, and enable the positive electrode active material to have reduced reactive activity, thereby inhibiting the oxidative decomposition of the electrolytic solution caused by the instability of the positive electrode active material, and reducing storage gas generation, and also cover the exposure point of the positive electrode current collector, thereby protecting the positive electrode current collector, especially the aluminum positive electrode current collector, from being corroded by the first compound.

It is well known that when formulating the electrolytic solution, lithium sulfonimide as a lithium salt is prone to oxidative decomposition when used in high-nickel lithium-ion batteries operating at high voltages, especially when stored at high temperature. However, the inventors of the present application surprisingly found that adding the above-mentioned second compound as an additive to the electrolytic solution can enable the positive electrode active material to have reduced reactive activity, inhibit the oxidative decomposition of the electrolytic solution on the positive electrode to some extent, and then inhibit the high-temperature gas production of the electrolytic solution, so that the electrolytic solution formulated with sulfonimide lithium salt has acceptable high-temperature storage performance even when used in high-nickel lithium-ion batteries operating at high voltage. The combined use of the above-mentioned second compound and the sulfonimide lithium salt as a primary lithium salt produces a synergistic effect. Therefore, the electrolytic solution according to the present application can effectively improve the power performance and high-temperature storage gas production performance of lithium-ion batteries simultaneously, and can even simultaneously improve the power performance and high-temperature storage gas production performance of high-nickel lithium-ion batteries operating at high charging voltages.

In some preferred embodiments, the second compound is present in an amount of 0.1 wt % to 3 wt %, for example, 0.1 wt % to 2 wt %, 0.3 wt % to 2 wt %, 0.5 wt % to 2 wt %, 0.1 wt % to 1 wt %, 0.3 wt % to 1 wt %, 0.5 wt % to 1 wt %, 0.1 wt % to 0.5 wt %, or 0.3 wt % to 0.5 wt %, relative to the total weight of the electrolytic solution. If the content of the second compound is too small, it is difficult to form a stable interface film on the cathode interface, and the decomposition of the electrolytic solution cannot be effectively suppressed. If the content of the second compound is too large, the power performance of the battery will deteriorate. Preferably, the content of the second compound is within each of the above ranges.

According to the present application, the relative ratio of the mass of the second compound to the total area of the current collector of the positive electrode plate will also affect performances of the battery. In some embodiments according to the present application, the ratio $M_{II}/S$ of the mass MII in g of the second compound to the total area S in $m^2$ of the positive current collector is in the range of 0.1 $g/m^2$ and 3.1 $g/m^2$. The above parameter represents the actual effective concentration of the second compound contained in the electrolytic solution inside the battery cell under actual working conditions. When the ratio is low, the second compound will not have the effect of inhibiting the primary lithium salt from corroding the aluminum foil. When the ratio is higher than 3.1, the second compound will decompose to form a thicker SEI film, which will increase the impedance of the battery cell and affect the powder performance of the battery cell.

According to the present application, the difference between the corrosion potential V1 of the first compound on the positive current collector and the reduction potential V2 of the second compound is also a parameter that affects battery performances. In some embodiments according to the present application, the difference $\Delta V$ between the corrosion potential of the first compound and the reduction potential of the second compound is between 2.7V and 4.2V.

When the potential difference ΔV is lower than 2.7V, the reduction products of the second compound will be deposited inside the negative electrode interface film that is close to the electrode side, which enables the reduction products of the second compound to fail to migrate to the positive electrode, cannot cover the exposure point of the aluminum current collector and thus cannot inhibit the corrosion of the aluminum foil caused by the first compound. When the potential difference ΔV is higher than 4.2V, the first compound cannot be reduced at the negative electrode interface where a relatively integral interface film has been formed to inhibit the decomposition of the electrolytic solution, so it cannot migrate to the positive electrode to protect the aluminum foil at all.

According to the present application, the corrosion potential V1 of the first compound on the positive electrode current collector is obtained by cyclic voltammetry. The reduction potential V2 of the second compound is obtained by linear sweep voltammetry.

The electrolytic solution according to the present application also comprises one or more organic solvents. The organic solvent is selected from one or more dimethyl carbonate, diethyl carbonate, dipropyl carbonate, ethyl methyl carbonate, methyl propyl carbonate, ethylene carbonate, propylene carbonate, ethylene carbonate, propylene carbonate, butylene carbonate, ethyl propyl carbonate, γ-butyrolactone, methyl formate, ethyl acetate, propyl acetate, methyl propionate, ethyl propionate, methyl propionate and tetrahydrofuran. In some preferred embodiments, the organic solvent is present in the electrolytic solution in a mass percentage of 65% to 85%.

The above-mentioned non-aqueous organic solvents have good thermal stability and electrochemical stability at higher temperatures and higher voltages, and provide a stable electrochemical environment for the electrical performance of high nickel lithium ion batteries operating at high voltages of 4.3V.

The above-mentioned electrolytic solution can be prepared according to the conventional methods in the art. The electrolytic solution may be obtained by mixing the organic solvent, the electrolyte lithium salt and optional additives uniformly. The addition order of each material is not particularly limited. For example, the electrolytic solution may be obtained by adding the electrolyte lithium salt and optional additives to the organic solvent and mixing them uniformly. Alternatively, the electrolytic solution can be obtained by adding the electrolyte lithium salt to the organic solvent first, and then adding the optional additives to the organic solvent separately or simultaneously.

The inventors of the present application surprisingly found that the lithium ion battery according to the present application can work at a high charging voltage and has a high energy density, and the power performance and high-temperature storage gas production performance of the battery are effectively improved, which is unpredictable prior to the present application. In contrast, the conventional low-nickel lithium-ion batteries work at a low operating voltage i.e. at a charge cut-off voltage V≤4.2V for battery cell and thus such lithium ion batteries do not have the technical problems described herein in the background. It is known that the low-nickel positive electrode active material has a relatively stable structure, has less charging delithiation at a low-voltage system, and produces fewer surface side reactions during the charging and discharging process. Therefore, the present application provides a high nickel lithium ion battery with a charge cut-off voltage of 4.3V or higher or a unit mass energy density of 250 wh/Kg. The lithium ion battery, in addition to the electrolytic solution as described above, further comprises a positive electrode plate, a separator and a negative electrode plate.

The positive electrode plate can be selected from various conventional positive electrode plates commonly used in the field, and its composition and preparation processes are well known in the art. For example, the positive electrode plate may comprise a positive current collector and a positive electrode active material layer disposed on the positive current collector, and the positive electrode active material layer may comprise a positive electrode active material, a binder, a conductive material and so on. Preferably, the positive electrode active material is a high nickel positive electrode active material represented by the structural formula $Li_aNi_{1-b}M_bO_2$, wherein a is in the range of 0.05 to 1.2, preferably 0.95 or more, more preferably 1.0, and b is in the range of 0 to 0.5 and M is selected from at least one element selected from iron, cobalt, manganese, copper, zinc, aluminum, boron, gallium, and magnesium. Preferably, $0.2 \leq b \leq 0.5$.

The negative electrode plate used in conjunction with the positive electrode plate can be selected from various conventional negative electrode plates commonly used in the art, and its composition and preparation processes are well known in the art. For example, the negative electrode plate may comprise a negative current collector and a negative active material layer disposed on the negative current collector, and the negative active material layer may comprise a negative active material, a binder, a conductive material and so on. The negative electrode active material is, for example, carbonaceous materials such as graphite (artificial graphite or natural graphite), conductive carbon black, and carbon fiber, metal or semi-metal materials such as Si, Sn, Ge, Bi, Sn, In, or alloys thereof, lithium-containing nitride or lithium-containing oxide, lithium metal or lithium aluminum alloy, and the like.

The separator used in the battery of the present application can be selected from various separators commonly used in the art.

The construction and preparation processes of these batteries are known per se.

Due to the use of the above-mentioned electrolytic solution, the battery can have improved high-temperature storage gas production performance and power performance.

Figure 1:
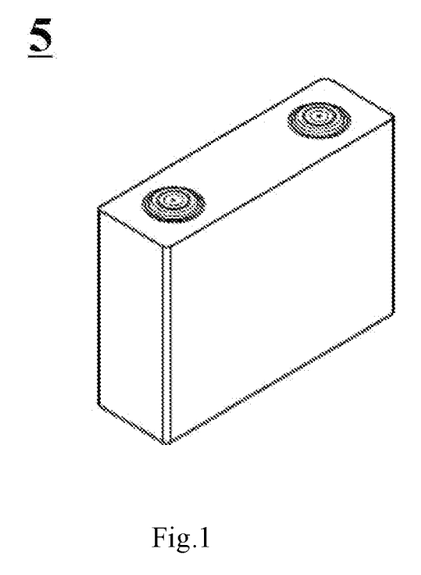
FIG. 1 is a perspective view of a lithium ion battery according to an embodiment of the present application.
Figure 2:
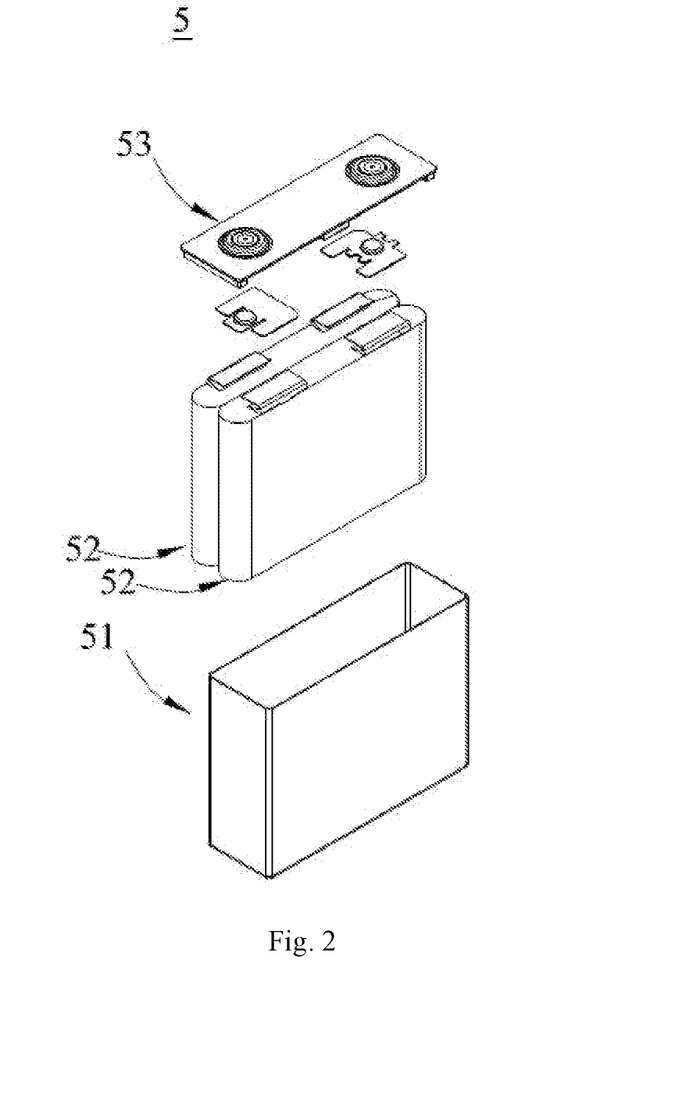
FIG. 2 is an exploded view of FIG. 1.

In a particular embodiment of the present application, the lithium ion has a structure as shown in the perspective view of a lithium ion battery 1 of FIG. 1. FIG. 2 is an exploded view of FIG. 1. Referring to FIG. 1 and FIG. 2, the lithium ion battery 5 includes a case 51, an electrode assembly 52, a top cover assembly 53, and an electrolytic solution (not shown). The electrode assembly 52 is packed in the case 51. There is no limitation to the number of electrode assembly 52, which may be one or more. The electrode assembly 52 comprises a positive electrode plate, a negative electrode plate, and a separator. The separator separates the positive electrode plate from the negative electrode plate. The electrolytic is injected into the case 51 and has soaked through the electrode assembly 52, the electrode assembly comprising, for example, a first electrode plate, a second electrode plate and a separator.

Please be noted that the lithium ion battery 5 shown in FIG. 1 is a can-type battery, but is not limited thereto, and the lithium ion battery 5 may be a pouch-type battery in which the case 51 is replaced by a metal plastic film and the top cover assembly 53 is removed.

Next, a battery module according to another aspect of the present application will be described.

Figure 3:
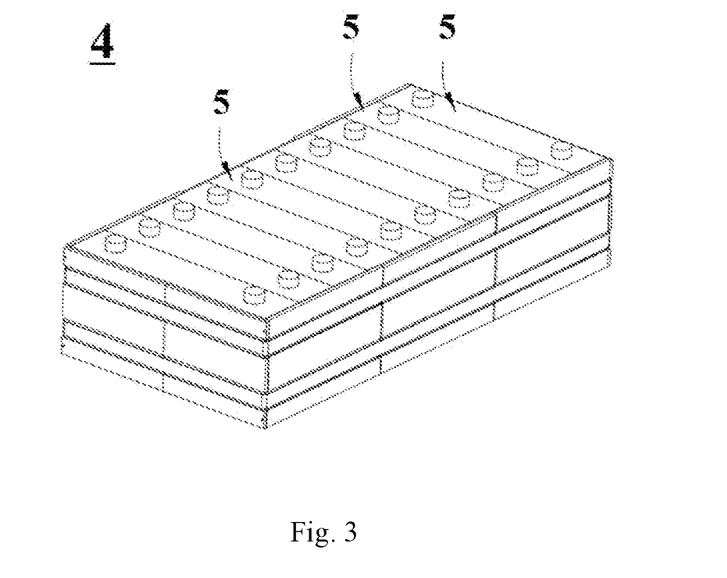
FIG. 3 is a perspective view of a battery module according to an embodiment of the present application.

FIG. 3 is a perspective view of a battery module 4 according to an embodiment of the present application.

The battery module 4 according to an embodiment of the present application comprises the lithium-ion battery 5 according to the present application.

Referring to FIG. 3, the battery module 4 includes a plurality of batteries 5. A plurality of lithium ion batteries 5 are arranged in the longitudinal direction. The battery module 4 can function as a power source or an energy storage device. The number of lithium ion battery 5 contained in the battery module 4 can be adjusted according to the application and capacity of the battery module 4.

Next, a battery pack according to a still another aspect of the present application will be described.

Figure 4:
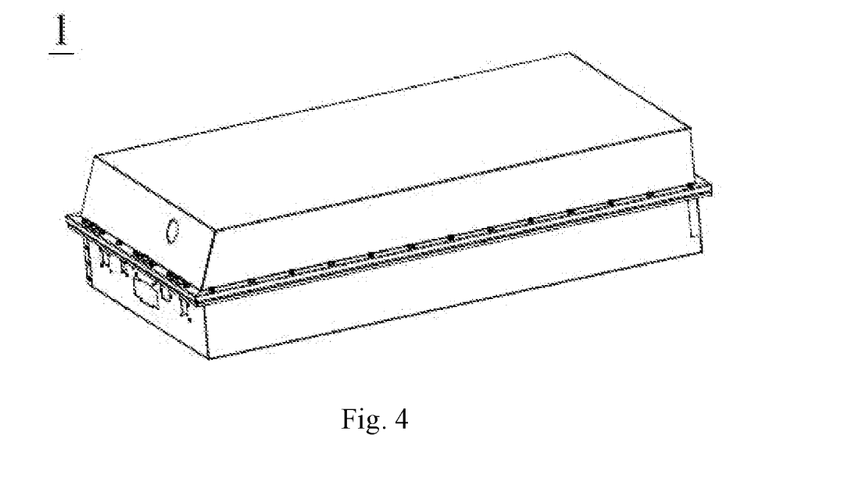
FIG. 4 is a perspective view of a battery pack according to an embodiment of the present application.
Figure 5:
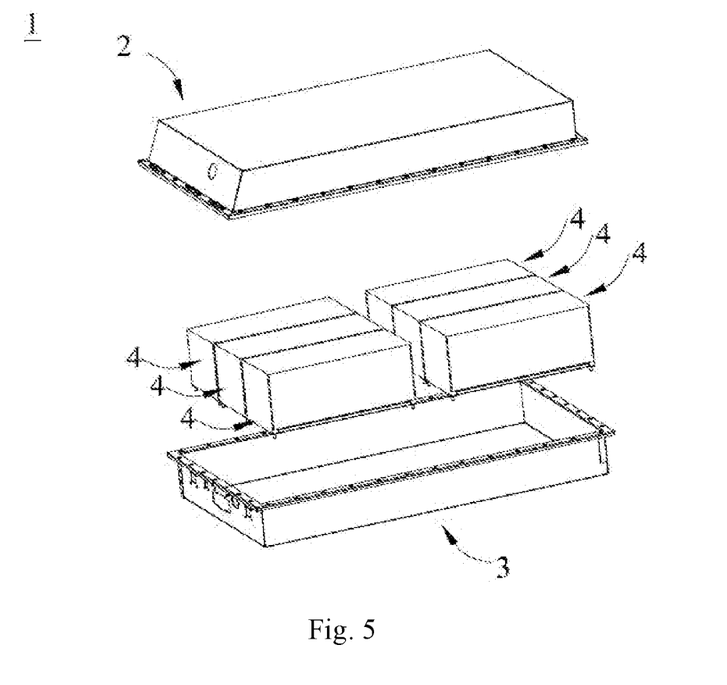
FIG. 5 is an exploded view of FIG. 4.

FIG. 4 is a perspective view of a battery pack 1 according to an embodiment of the present application. FIG. 5 is an exploded view of FIG. 4.

The battery pack 1 according to the present application comprises the battery module 4 according to an embodiment of the present application.

Specifically, referring to FIG. 4 and FIG. 5, the battery pack 1 comprises an upper cabinet body 2, a lower cabinet body 3, and a battery module 4. The upper cabinet body 2 and the lower cabinet body 3 are assembled together to form a space in which the battery module 4 is packed. The battery module 4 is placed in the space formed by assembling the upper cabinet body 2 and the lower cabinet body 3 together. The battery module 4 comprises an output passing through one or both of the upper cabinet body 2 and the lower cabinet body 3 to supply power to the outside or to be charged from the outside. The number and arrangement of the battery modules 4 contained in the battery pack 1 can be determined according to actual needs.

Next, an apparatus according to still another aspect of the present application will be described.

Figure 6:
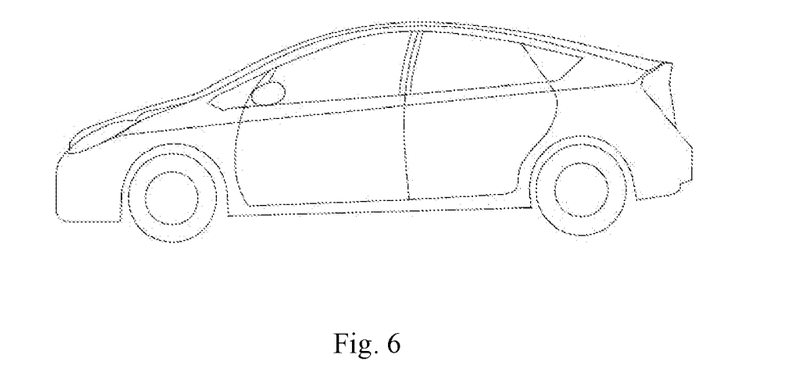
FIG. 6 is a schematic view showing an apparatus with a lithium ion battery as a power source according to an embodiment of the present application.

FIG. 6 is a schematic view showing an apparatus with a lithium ion battery as a power source according to an embodiment of the present application.

The apparatus according to the present application comprises the lithium ion battery 5 according to an embodiment of the present application, and the lithium ion battery 5 can be used as a power source of the apparatus. In FIG. 6, the apparatus with the lithium ion battery 5 is an electric car. Of course, without limited thereto, the apparatus with the lithium ion battery 5 may be any other electric vehicles such as, an electric bus, an electric tram, an electric bicycle, an electric motorcycle, an electric scooter, an electric golf cart, an electric truck, electric ships, electric tools, electronic equipment and energy storage systems. The electric vehicle can be a pure electric vehicle, a hybrid electric vehicle, or a plug-in hybrid electric vehicle. Of course, according to the actual form of use, the apparatus according to the present application may comprises the battery module 4 as described in the present application. Of course, the apparatus according to the present application may also comprises the battery pack 1 as described in the present application.

Examples

In order to make the object, technical solutions, and beneficial technical effects of the present application clearer, the following further describes the present application in detail with reference to examples. However, it should be understood that the examples of the present application are only for illustrating the present application, not for limiting the present application, and the examples of the application are not limited to the particular examples given in the specification. The examples in which the particular experimental conditions are not specified adopt the conventional conditions or the conditions recommended by material suppliers or equipment suppliers.

1. Preparation Process (1) Preparation of Electrolytic Solution

In a glove box filled with argon gas (water content <10 ppm, oxygen content <1 ppm), lithium sulfonimide salt was used as a primary salt, lithium hexafluorophosphate was used as a secondary salt, and ethanedisulfonic anhydride or 1,3-malonic anhydride was used as the second compound. The above three materials were added to an non-aqueous organic solvent in a certain mass ratio in which the non-aqueous organic solvent consisted of ethylene carbonate (EC) and diethyl carbonate (DEC) in a ratio of 30:70. After the lithium salts were completely dissolved, an appropriate amount of the additive was added. After stirring uniformly, an electrolytic solution with a lithium salt concentration of 1.0 mol/L was obtained.

In Examples 1-11 and Comparative Examples 1-5, the lithium salt and additive as used and their amounts were shown in Table 1, in which the concentration of the lithium salt is calculated based on the total volume of the electrolytic solution, and the content of the additive is a mass percentage as calculated based on the total mass of the electrolytic solution.

(2) Preparation of Positive Electrode Plate:

The positive electrode active material $LiNi_{0.8}Co_{0.1}Mn_{0.1}O_2$, the conductive agent Super P, and the binder polyvinylidene fluoride (PVDF) were made into a positive electrode slurry in N-methylpyrrolidone (NMP). The solid content of the positive electrode slurry was 50 wt %, and the mass ratio of $LiNi_{0.8}Co_{0.1}Mn_{0.1}O_2$, Super P, PVDF in solid was 8:1:1. The positive electrode slurry was coated on the current collector aluminum foil and dried at 85° C. followed by cold pressing, trimming, slicing and slitting, and then further dried under vacuum at 85° C. for 4 h, thereby obtaining a positive electrode plate.

(3) Preparation of Negative Electrode Plate:

The negative electrode active material graphite, the conductive agent Super P, the thickener CMC, and the binder styrene butadiene rubber (SBR) were mixed uniformly in deionized water to form a negative electrode slurry. The solid content in the negative electrode slurry was 30 wt %, and the mass ratio of graphite, Super P, CMC and binder styrene butadiene rubber (SBR) in solid was 80:15:3:2. The negative electrode slurry was coated on the current collector copper foil and dried at 85° C. followed by cold pressing, trimming, slicing and slitting, and then further dried under vacuum at 120° C. for 12 h, thereby obtaining a negative electrode plate.

(4) Preparation of Separator

Polyethylene film (PE) in a 16 micron thickness was used as the separator.

(5) Preparation of Lithium Ion Battery:

The prepared positive electrode plate, the separator, and the negative electrode plate were stacked in order, so that the separator was disposed between the positive and negative electrode plates for isolation. After winding, a bare core was obtained. Having had a tab welded on, the bare core was packed in an outer packaging in which the electrolytic solution prepared above was injected followed by packing, standing, forming, shaping and testing the capacity, thereby completing the preparation of the lithium ion battery. The soft-pack lithium-ion battery had a thickness of 4.0 mm, a width of 60 mm, and a length of 140 mm.

2. Performance Test (1) Test for High Temperature Gas Production Performance of Lithium Ion Battery At room temperature (25° C.), the lithium-ion battery was charged to 4.3V at a constant current of 1 C, and then charged to a current of 0.05 C at a constant voltage of 4.3V. After the battery was fully charged, the water exclusion method was used to test the initial volume of the battery. And then the battery was stored in an oven at 80° C. for 24 hours and then removed. Let the removed battery stand at room temperature for 60 minutes. The volume of the battery was measured by the water exclusion method within 60 minutes after the battery was cooled to room temperature.

Following above storage steps, the storage test were carried out until 30 days. On the basis of the battery volume tested before storage, the volume expansion rate of the battery with different storage periods was calculated. The volume expansion rate (%) of lithium-ion battery after storage for n days at 80° C.=(the difference of the battery volume measured after storage for n days and the battery volume measured before storage relative to the battery volume measured before storage.

(2) Test for Powder Performance of Lithium Ion Battery

At room temperature, the lithium-ion battery was charged to 4.3V with a constant current of 1 C, and then charged with a constant voltage of 4.3V to a current of 0.05 C. After the battery was fully charged, let it stand for 5 min, and then discharge it at 1 C for 30 min so that the quantity of battery charge was 50% SOC, and then let it stand for 5 min. Adjust the temperature to −20° C., let it stand for 1 hour, and then record the voltage V1 of the battery. The battery was discharged at 0.4 C for 15 s, and the voltage V2 after pulse discharge was recorded. DCR at 50% SOC=(V1-V2)/I in which I=0.4 C.

TABLE 1 composition of electrolytic solution

| | Positive material Material | Primary salt Type | Content (M) | Secondary salt Type | Content (M) | Molar ratio of primary to secondary salts | Second compound Type | Ratio of absolute mass to surface area of current collector g/m$^2$ |
|---|---|---|---|---|---|---|---|---|
| Ex. 1 | LiNi$_{0.8}$Co$_{0.1}$Mn$_{0.1}$O$_2$ | lithium bis(fluorosulfonyl)imide | 0.9 | LiPF$_6$ | 0.1 | 9:1 | ethanedisulfonic anhydride | 0.31 |
| Ex. 2 | LiNi$_{0.8}$Co$_{0.1}$Mn$_{0.1}$O$_2$ | lithium bis(fluorosulfonyl)imide | 0.8 | LiPF$_6$ | 0.2 | 8:2 | ethanedisulfonic anhydride | 0.31 |
| Ex. 3 | LiNi$_{0.8}$Co$_{0.1}$Mn$_{0.1}$O$_2$ | lithium bis(fluorosulfonyl)imide | 0.7 | LiPF$_6$ | 0.3 | 7:3 | ethanedisulfonic anhydride | 0.31 |
| Ex. 4 | LiNi$_{0.8}$Co$_{0.1}$Mn$_{0.1}$O$_2$ | lithium bis(fluorosulfonyl)imide | 0.6 | LiPF$_6$ | 0.4 | 6:4 | ethanedisulfonic anhydride | 0.31 |
| Ex. 5 | LiNi$_{0.8}$Co$_{0.1}$Mn$_{0.1}$O$_2$ | lithium bis(fluorosulfonyl)imide | 0.7 | LiPF$_6$ | 0.3 | 7:3 | ethanedisulfonic anhydride | 3.1 |
| Ex. 6 | LiNi$_{0.8}$Co$_{0.1}$Mn$_{0.1}$O$_2$ | lithium bis(fluorosulfonyl)imide | 0.7 | LiPF$_6$ | 0.3 | 7:3 | ethanedisulfonic anhydride | 0.1 |
| Ex. 7 | LiNi$_{0.8}$Co$_{0.1}$Mn$_{0.1}$O$_2$ | lithium methylsulfonyl trifluoromethanesulfonyl imide | 0.7 | LiBF$_4$ | 0.3 | 7:3 | 1,3-malonic anhydride | 1.04 |
| Ex. 8 | LiNi$_{0.8}$Co$_{0.1}$Mn$_{0.1}$O$_2$ | lithium methylsulfonyl trifluoromethanesulfonyl imide | 0.7 | LiPF$_6$ | 0.3 | 7:3 | 1,3-malonic anhydride | 2.08 |
| Ex. 9 | LiNi$_{0.5}$Co$_{0.2}$Mn$_{0.3}$O$_2$ | lithium bis(fluorosulfonyl)imide | 0.8 | LiPF$_6$ | 0.2 | 8:2 | 1,3-malonic anhydride | 0.52 |
| Ex. 10 | LiNi$_{0.6}$Co$_{0.2}$Mn$_{0.2}$O$_2$ | lithium bis(fluorosulfonyl)imide | 0.8 | LiPF$_6$ | 0.2 | 8:2 | 1,3-malonic anhydride | 0.52 |
| Ex. 11 | LiNi$_{0.5}$Mn$_{1.5}$O$_4$ | lithium bis(fluorosulfonyl)imide | 0.8 | LiPF$_6$ | 0.2 | 8:2 | 1,3-malonic anhydride | 0.52 |
| CEx. 1 | LiNi$_{0.8}$Co$_{0.1}$Mn$_{0.1}$O$_2$ | lithium methylsulfonyl trifluoromethanesulfonyl imide | / | LiPF$_6$ | 1 | 0:1 | 1,3-malonic anhydride | 0.31 |
| CEx. 2 | LiNi$_{0.8}$Co$_{0.1}$Mn$_{0.1}$O$_2$ | lithium methylsulfonyl trifluoromethanesulfonyl imide | 0.1 | LiPF$_6$ | 0.9 | 1:9 | 1,3-malonic anhydride | 0.31 |
| CEx. 3 | LiNi$_{0.8}$Co$_{0.1}$Mn$_{0.1}$O$_2$ | lithium methylsulfonyl trifluoromethanesulfonyl imide | 0.7 | LiPF$_6$ | 0.3 | 7:3 | 1,3-malonic anhydride | 0 |
| CEx. 4 | LiNi$_{0.8}$Co$_{0.1}$Mn$_{0.1}$O$_2$ | lithium methylsulfonyl trifluoromethanesulfonyl imide | 0.7 | LiPF$_6$ | 0.3 | 7:3 | ethanedisulfonic anhydride | 0.01 |
| CEx. 5 | LiNi$_{0.8}$Co$_{0.1}$Mn$_{0.1}$O$_2$ | lithium methylsulfonyl trifluoromethanesulfonyl imide | 0.7 | LiPF$_6$ | 0.3 | 7:3 | ethanedisulfonic anhydride | 4 |

In above table 1, / means that this kind of substance is not added.

TABLE 2 performances of battery

| | volume expansion rate (%) of lithium-ion battery after storage for 10 days at 80° C. | Low temperature DCR (mohm) |
|---|---|---|
| Ex 1 | 7% | 140 |
| Ex 2 | 10% | 163 |
| Ex 3 | 15% | 179 |
| Ex 4 | 19% | 200 |
| Ex 5 | 13% | 227 |
| Ex 6 | 17% | 151 |
| Ex 7 | 14% | 171 |
| Ex 8 | 12% | 181 |
| Ex 9 | 5% | 170 |
| Ex 10 | 6% | 130 |
| Ex 11 | 6% | 124 |
| CEx 1 | 28% | 270 |
| CEx 2 | 25% | 240 |
| CEx 3 | 32% | 300 |

TABLE 2-continued performances of battery

| | volume expansion rate (%) of lithium-ion battery after storage for 10 days at 80° C. | Low temperature DCR (mohm) |
|---|---|---|
| CEx 4 | 27% | 290 |
| CEx 5 | 20% | 200 |

It was shown from the test results in Table 2 that compared with the high-temperature storage gas production performance and the low-temperature DCR of Comparative Examples 1-5, the overall performances of Examples 1-11 were improved. The above results showed that not only did the combination of the first compound and the second compound improve the power performance of the electrolytic solution and inhibit the corrosion of the aluminum foil, but it also improved the high-temperature storage performance.

In Comparative Example 1 and Comparative Example 2, the lithium sulfonimide salt did not act as the primary main salt, the electrolytic solution had a relatively low conductivity, and poor stability so that the electrolytic solution had poor storage gas production and power performance.

In Comparative Example 3 and Comparative Example 4, although the lithium sulfonimide salt was used as the primary salt, the electrolytic solution did not comprise the second compound or the ratio of the mass of the second compound in the electrolytic solution to the total area of the positive electrode current collector was too small. Therefore, the corrosion effect of the primary salt on the aluminum foil was not effectively suppressed. The electrolytic solution was prone to produce side reactions at the interface of the corroded hole and generate gas and decomposition product with poor conductivity, thereby negatively affecting the power performance.

In Comparative Example 5, the ratio of the mass of the second compound to the total area of the positive electrode current collector was too high. Although the second compound effectively inhibited the corrosive effect of the sulfonimide salt on the current collector, the reduction and decomposition products of the second compound formed a thick film on the negative electrode, and there were more decomposition products that migrated to the surface of the positive electrode. Thus, the film formed on the positive electrode was also thicker, thereby enabling the interface impedance of the positive and negative electrodes to be higher and the electrochemical polarization to be higher, which in turn induced the decomposition of the electrolytic solution so that the gas production increased, and the impedance increased.

The above results shows that when the first compound and the second compound are used in combination and meet the above mentioned conditions, the overall performance of the battery may be greatly improved.

It will be apparent to those skilled in the art that the present application may be modified and varied in accordance with the above disclosure and teachings. Accordingly, the present application is not limited to the specific embodiments disclosed and described above, and modifications and variations of the present application are intended to be included within the scope of the claims of the present application. In addition, although some specific terminology is used in this specification, these terms are for convenience of illustration only and are not intended to limit the present application in any way.

The invention claimed is:
1. A lithium ion battery, comprising: a positive electrode plate, a negative electrode plate, a separator disposed between the positive electrode plate and the negative electrode plate, and an electrolytic solution, the positive electrode plate including a positive electrode current collector and a positive electrode active material layer provided on at least one side of the positive electrode current collector, and the electrolytic solution including an organic solvent, a lithium salt and an additive,
wherein the lithium salt comprises a primary lithium salt, the primary lithium salt is a first compound in an amount of 30% or more relative to the total molar amount of the lithium salt, and the first compound has a structure represented by the following formula I:

(Formula I)

in which formula I, $R_1$ and $R_2$ each independently represent a fluorine atom, a fluoroalkyl group having 1-20 carbon atoms, or a fluoroalkoxy group having 1-20 carbon atoms, and wherein the additive comprises a second compound represented by the following formula II,

(Formula II)

in which formula II, $R_3$ represents an alkylene group having 2-4 carbon atoms, a fluoroalkylene group having 2-4 carbon atoms, an alkyl-substituted alkylene group having 2-4 carbon atoms, an alkenylene group having 2-4 carbon atoms, a fluoroalkenylene group having 2-4 carbon atoms, an alkyl-substituted alkenylene group having 2-4 carbon atoms, an arylene group having 6-14 carbon atoms, and a fluorinated arylene group having 6-14 carbon atoms or an alkyl-substituted arylene group having 6-14 carbon atoms, and
wherein the positive electrode active material layer comprises a positive electrode active material represented by the structural formula $Li_aNi_{1-b}M_bO_2$, wherein a is in the range of 0.85 to 1.2, preferably 0.95 or more, b is in the range of 0 to 0.5, and M is at least one element selected from iron, cobalt, manganese, copper, zinc, aluminum, boron, gallium, and magnesium;
wherein a ratio $M_{II}/S$ of a mass $M_{II}$ (g) of the second compound to a total area S (m$^2$) of the positive electrode current collector is in the range of 0.1 g/m$^2$ to 3.1 g/m$^2$; and
wherein the lithium salt further comprises a secondary lithium salt and the secondary lithium salt is selected from one or more of lithium hexafluorophosphate, lithium tetrafluoroborate, and lithium trifluoromethanesulfonate, lithium hexafluoroarsenate, lithium bisoxalate borate and lithium perchlorate, preferably selected from one or two of lithium hexafluorophosphate and lithium tetrafluoroborate, and more preferably selected from lithium hexafluorophosphate; and
wherein a molar ratio of the primary lithium salt and the secondary lithium salt is in the range of 5:5 to 9:1, preferably in the range of 6:4 to 8:2.

2. The lithium ion battery according to claim 1, wherein the first compound is selected from one or more of lithium bis(fluorosulfonyl)imide, lithium fluorosulfonyl trifluoromethylsulfonyl imide, lithium bis(trifluoromethylsulfonyl)imide, lithium methylsulfonyl trifluoromethylsulfonyl imide, lithium trifluoromethylsulfonyl pentafluoroethylsulfonyl imide, lithium bis(pentafluoroethylsulfonyl) imide, LiN(SO$_2$OCH$_2$CF$_3$)$_2$, LiN(SO$_2$OCH$_2$CF$_2$CF$_3$)$_2$, LiN(SO$_2$OCH$_2$CF$_2$CF$_2$H)$_2$, LiN[(SO$_2$OCH(CF$_3$)$_2$], preferably selected from one or two of lithium bis(fluorosulfonyl)imide and lithium methylsulfonyl trifluoromethanesulfonyl imide, and more preferably selected from lithium bis(fluorosulfonyl)imide.

3. The lithium ion battery according to claim 1, wherein the second compound is selected from one or more of the following compounds:

4. The lithium ion battery according to claim 1, wherein the second compound is present in an amount of 0.1 wt % to 3 wt % based on the total weight of the electrolytic solution.

5. The lithium ion battery according to claim 1, wherein the organic solvent is selected from one or more of dimethyl carbonate, diethyl carbonate, dipropyl carbonate, ethyl methyl carbonate, methyl propyl carbonate, ethylene carbonate, propylene carbonate, ethylene carbonate, propylene carbonate, butylene carbonate, ethyl propyl carbonate, γ-butyrolactone, methyl formate, ethyl acetate, propyl acetate, methyl propionate, ethyl propionate, methyl propionate and tetrahydrofuran, preferably, the organic solvent is present in the electrolytic solution in a mass percentage of 65%-85%.

6. The lithium ion battery according to claim 1, wherein a difference $\Delta V = V1 - V2$ between a corrosion potential V1 of the first compound to the positive current collector and a reduction potential V2 of the second compound satisfies $2.7V \leq \Delta V \leq 4.2V$.

7. The lithium ion battery according to claim 1, wherein the battery has a charge cut-off voltage of 4.3V or higher, or has an energy density per unit mass of 250 wh/Kg.

8. A battery module comprising the lithium ion battery as claimed in claim 1.

9. An apparatus comprising the lithium ion battery as claimed in claim 1, wherein the lithium ion battery is used as a power source of the apparatus; preferably, the apparatus comprising electric vehicles, hybrid electric vehicles, plug-in hybrid electric vehicles, electric bicycles, electric scooters, electric golf carts, electric trucks, electric ships, or energy storage systems.

* * * * *